United States Patent [19]
Ramachandran et al.

[11] Patent Number: 4,849,537
[45] Date of Patent: Jul. 18, 1989

[54] PROCESS FOR THE PRODUCTION OF NITRILES

[75] Inventors: Ramakrishnan Ramachandran, Allendale; Donald L. MacLean, Annandale; Donald P. Satchell, Jr., Summit, all of N.J.

[73] Assignee: The BOC Group, Inc., Murray Hill, N.J.

[21] Appl. No.: 215,859

[22] Filed: Jul. 6, 1988

Related U.S. Application Data

[63] Continuation-in-part of Ser. No. 154,157, Feb. 9, 1988, abandoned.

[51] Int. Cl.$^4$ ............................................. C07C 120/14
[52] U.S. Cl. ...................................... 558/319; 558/320
[58] Field of Search ................................. 558/319, 320

[56] References Cited

U.S. PATENT DOCUMENTS

| | | | |
|---|---|---|---|
| 3,161,670 | 12/1964 | Adams et al. | 558/320 |
| 3,176,444 | 4/1965 | Kiyonaga | 55/26 |
| 3,591,620 | 7/1971 | Yoshino et al. | 260/465.3 |
| 4,070,393 | 1/1978 | Angstadt et al. | 558/319 X |
| 4,246,192 | 1/1981 | Pujado | 558/320 |
| 4,335,056 | 6/1982 | Callahan et al. | 260/465.3 |
| 4,498,910 | 2/1985 | Benkmann | 55/18 |
| 4,609,502 | 9/1986 | Khoobiar et al. | 260/465.3 |
| 4,754,049 | 6/1988 | Khoobiar et al. | 558/319 X |

OTHER PUBLICATIONS

Gates, et al.; "Chemistry of Catalytic Processes", (1979), McGraw-Hill, pp. 349-350 and 380 to 384.
Thomas, "Catalytic Processes and Pronen Catalysts", (1970), Academic Press, pp. 118-119.
Pujado, et al.; "Catalytic Conversion of LPG" (1986), American Inst. of Chem. Eng., pp. 1-19, drawings & tables.

Primary Examiner—Joseph Paul Brust
Attorney, Agent, or Firm—Carol A. Nemetz; R. Hain Swope; Larry R. Cassett

[57] ABSTRACT

An improved process is provided for the production of nitriles from hydrocarbons by reaction with oxygen, air or gas-enriched in relative to an air, and ammonia, in the presence of an ammoxidation catalyst. An alkane, e.g. propane, is converted to an alkene in a multistage dehydrogenator. The product stream is withdrawn from a reactor in the dehydrogenator other than the first and the last reactor and introduced into an ammoxidation reactor. The product is recovered in a conventional quench tower. The gaseous effluent from the quench tower is treated in a pressure swing adsorption unit to form a gas stream containing the unreacted alkane and alkene as well as a minor amount of oxygen. The gas stream, which may or may not contain hydrogen depending on the absorbent in the pressure swing adsorption unit, is introduced into the reactor in the dehydrogenator following that from which the product stream was withdrawn. The effluent from the last reactor in the dehydrogenator is introduced into: the first reactor; an intermediate reactor wherein the alkene concentration closely approximates the effluent or the ammoxidation reactor. The subject process is particularly efficient utilizing oxygen-enriched air in the reactor feed. A particularly preferred pressure swing adsorption system for use in the subject process comprises two parallel pressure swing adsorption units containing different adsorbents such that the gas stream formed in one contains all of the hydrogen in the gas phase from the quench tower. The feed to the pressure swing adsorption units is divided disproportionately so that the combined pressure swing adsorption effluent recycle streams contain the optimum concentration of hydrogen for the dehydrogenator.

18 Claims, 4 Drawing Sheets

PROCESS FOR THE PRODUCTION OF NITRILES

RELATED APPLICATIONS

This application is a continuation-in-part of U.S. Patent application Ser. No. 154,157, filed Feb. 9, 1988, now abandoned.

The present invention is directed to a process for producing nitriles from alkanes, an oxygen-containing gas and ammonia in the presence of a suitable catalyst under conditions which achieve high efficiency and selectivity toward the desired product.

BACKGROUND OF THE INVENTION

The production of nitriles by ammoxidation of an appropriate alkene in the presence of a suitable catalyst is well known. The production of acrylonitrile, for example, from a gaseous feed of propylene, ammonia and air is described by Bruce E. Gates et al in *Chemistry of Catalytic Processes*, McGraw-Hill (1979), pp. 380-384.

The feed is sent to an ammoxidation reactor where, in the presence of a suitable catalyst, acrylonitrile is produced along with lesser amounts of other nitrogen-containing compounds. The effluent from the ammoxidation reaction is quenched with water and the desired products are obtained in the liquid phase. The gas phase by-products, typically oxygen, carbon dioxide, carbon monoxide, nitrogen and unreacted hydrocarbon, are combined with natural gas and sent to a boiler for combustion as disclosed, for example, in Yoshino et al., U.S. Pat. No. 3,591,620 and Callahan et al., U.S. Pat. No. 4,335,056.

More recently, Khoobiar et al., in U.S. Pat. No. 4,609,502 disclosed a cyclic process for producing acrylonitrile using propane as a starting material which is initially dehydrogenated catalytically in the presence of steam to form propylene. This is in contract to most conventional dehydrogenation processes which avoid steam primarily due to the costs involved. After ammoxidation, the effluent is quenched, the desired product removed, and the off-gases, including propylene and propane, are sent to an oxidation reactor to remove oxygen by selective reaction with hydrogen to form water varpor. The gas mixture exiting the selective oxidation reactor includes substantial amounts of methane, ethane and ethylene, which are by-products of dehydrogenation, and unreacted propylene in addition to carbon oxides. As an option, this gas mixture is slit and a portion is sent to a separator which removes only carbon dioxide. A portion of the effluent from the separator is purged to remove light hydrocarbons. The nonpurged stream is mixed with the remainder of the oxidator effluent, fresh propane and steam, if necessary, sent to the dehydrogenator where the propane is converted to propylene. Another option is to cool and liquify the $C_3$ hydrocarbons therefrom and then vaporize them prior to recycle.

The aforementioned process suffers from several disadvantages. For example, there is no practical way to selectively remove by-products of propane dehydrogenation, such as methane, ethane, ethylene and the like, thereby preventing their accumulation in the system other than by removing them in a purge stream. The removal of these gases in a purge stream will result in a loss of the circulating propane and propylene, thus causing a significant decrease in the yield of propylene. As mentioned above, propane and propylene can be recovered from the stream prior to venting. This requires additional refrigeration apparatus to cool and liquify the propylene and propane. The separated $C_3$ hydrocarbons must be vaporized prior to recycle. These operations add to the capital costs and power requirements of the process.

Another disadvantage of the Khoobiar et al process stems from the use of the selective oxidation reactor to treat the gaseous effluent from the quencher. The gases exiting the quencher are at ambient temperature and must be heated prior to introduction into the oxidation reactor in order to promote oxygen removal. Because there is a significant amount of oxygen in the quencher effluent, the heat of reaction generated in the oxidation reactor can result in excessive temperatures in the system. There are three options to alleviate this problem. First, the amount of oxygen entering the oxidation reactor can be reduced by other means. Second, multiple reactors can be utilized with a cooling means between each pair of reactors. Third, a portion of the effluent from the reactor is passed through a cooling means and recycled to the feed to reduce the internal temperature of the reactor. None of these measures is attractive from the viewpoint of cost and efficiency.

The oxidation reactor in the Khoobiar et al process is operated with oxidation catalysts such as noble metals (e.g., platinum). Olefins and carbon monoxide, which are generated in the dehydrogenation reactor, are known to deactivate these catalysts, as disclosed in *Catalytic Processes and Proven Catalysts*, Charles L. Thomas, Academic Press (1970) pp. 118-119. Accordingly, multiple oxidation reactors must be used to allow for frequent regeneration of the catalyst which represents yet another addition to production costs (U.S. Pat. No. 4,609,502, column 4, lines 51-56).

It is therefore apparent that the industry is still searching for a cost effective process of converting hydrocarbons into nitriles. Applicants have discovered a process which is cost effective and in which the disadvantages of the aforementioned systems are substantially reduced or eliminated. Moreover, in comparison to conventional processes, the thermal requirements of Applicants' process are markedly reduced.

SUMMARY OF THE INVENTION

A process is disclosed for the production of nitriles comprising converting a gaseous alkane to the corresponding alkene in a multistage dehydrogenator comprising at least three discrete reactors. The product stream containing the alkene and unreacted alkane is withdrawn from a reactor intermediate the first and last reactors. The feed stream is passed through heating means to raise the temperature thereof between each of the discrete reactors up to and including the reactor from which the product stream is withdrawn. The catalyst in the dehydrogenator is passed through all reactors, regenerated and recycled to the first reactor. The alkene is reacted in an ammoixidation reactor with an oxygen-containing gas, preferably oxygen-enriched air, ammonia gas in the presence of a suitable catalyst to form the desired product. The product stream is quenched with a liquid to form a liquid phase containing the desired product and a gas phase which is passed under pressure into a pressure swing adsorption unit to remove carbon oxides, oxygen, nitrogen when present, and lower hydrocarbons therefrom. The product stream from the pressure swing adsorption unit is recycled into the reactor of the multistage dehydrogenator immediately following that from which the product stream is withdrawn and passed through that reactor and any subsequent reactor. The effluent from the last reactor may be introduced to the first reactor, to an intermediate reactor or directly to the ammoxidation reactor. A hydrogen recovery means may be utilized to remove hydrogen from the dehydrogenator product stream for recycle.

DESCRIPTION OF THE PREFERRED EMBODIMENTS

The process of this invention is applicable to the synthesis of nitriles. In each instance, an alkene, which has been formed by the dehydrogenation of the corresponding alkane, is reacted with an oxygen-containing gas comprising pure oxygen, air, or a gas-enriched in oxygen relative to air in the presence of a suitable catalyst. The term "suitable catalyst" indicates a catalyst that will catalyze the production of the desired product under the conditions utilized in the reactor. In the subject process, the catalyst is an ammoxidation catalyst. These catalysts and their use are conventional and well known to one of ordinary skill in the art.

Illustrative of products, and their respective starting gaseous alkanes, which can be advantageously produced by the method of this invention are acrylonitrile from propane, methacrylonitrile from isobutane, and the like. In the interest of brevity, the subject process will be described with reference to the production of acrylontrile from propane, but is in no way intended to be limited thereto.

Figure 1:
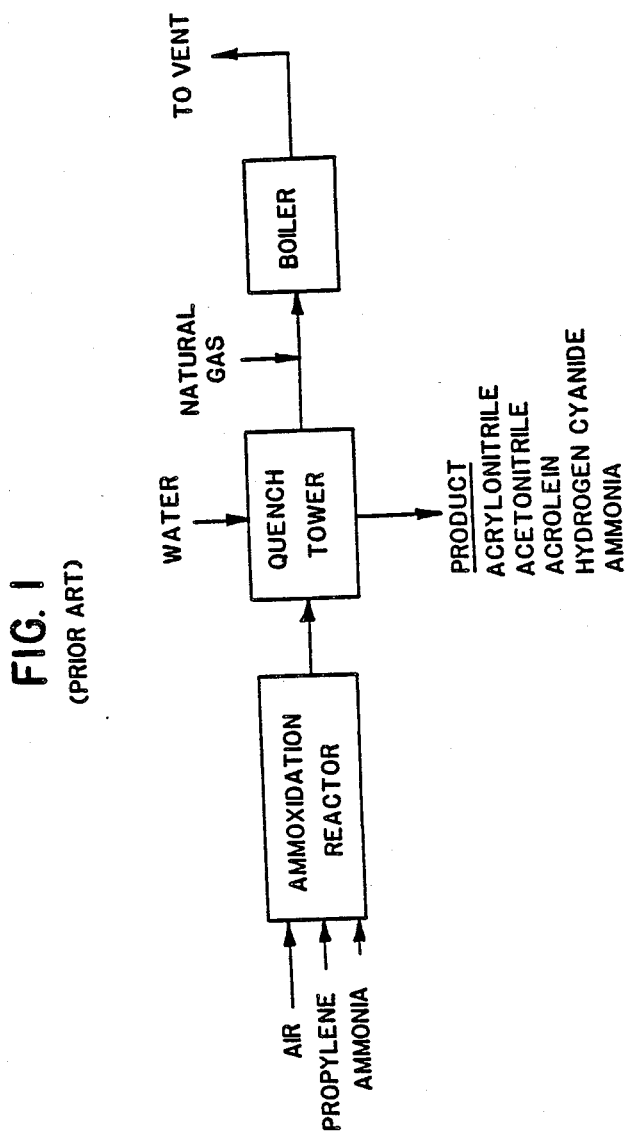
FIG. 1 illustrates in a block diagram a present conventional process of producing acrylonitrile from propylene.

Turning to the drawings, a process currently utilized commercially to produce acrylonitrile is illustrated in FIG. 1. Propylene, ammonia and air are fed into a conventional reactor containing a suitable ammoxidation catalyst. The reactor may be of any conventional fixed or fluidized bed design, typically the latter. Such processes, which do not involve a recycle step, utilized air or oxygen-enriched air in the reactor feed, although air is normally used for reasons of economy. The oxygen concentration in the reactor feed is not considered to be critical in regard to the accumulation of other gases, primarily nitrogen, in the system due to the lack of recycle. Those skilled in the art are aware that the oxygen content in the feed of such a process must be regulated in regard to other aspects of the process.

The reactor product gases are cooled in a heat exchanger, not shown, to form steam and then passed to a water quench column or tower to dissolve the products, i.e. acrylonitrile, acetonitrile, acrolein and hydrogen cyanide, as well as unreacted ammonia. The acrylonitrile is subsequently recovered from the aqueous solution by conventional methods. The off-gases from the quench tower are combined with natural gas and combusted in a boiler to generate steam. The off-gases of the boiler are vented. Since there is no recycle provided in such a process, the yield of acrylonitrile realized is directly related to the efficiency of the reactor.

Figure 2:
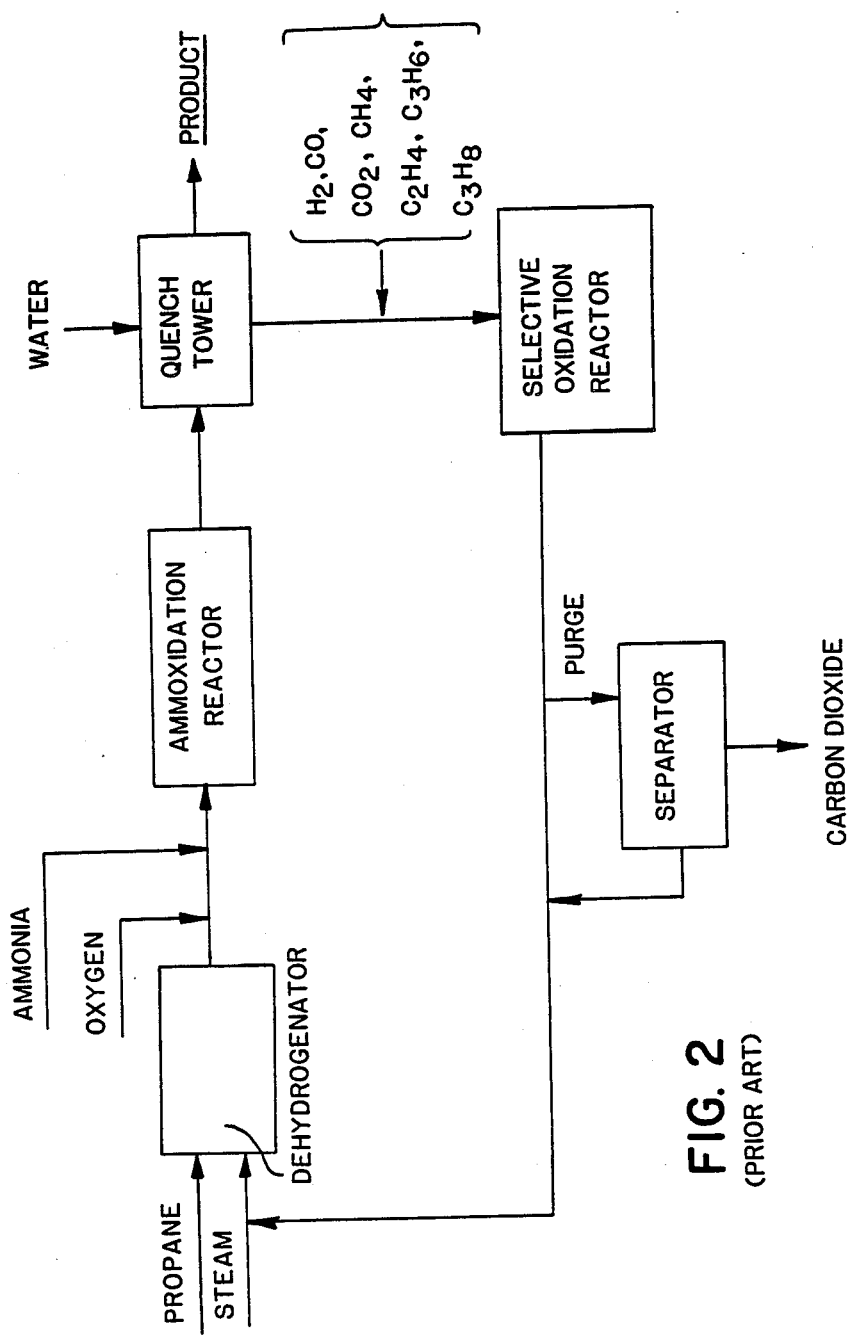
FIG. 2 illustrates in a block diagram a prior art process of producing acrylonitrile utilizing a recycle step.

FIG. 2 illustrates the cyclic process for producing acrylonitrile disclosed in Khoobiar et al U.S. Pat. No. 4,609,502. In this process, propane and steam are fed into a dehydrogenator to form propylene which is then mixed with pure oxygen and ammonia and fed into an ammoxidation reactor such as described in FIG. 1. The product is fed to an aqueous quench tower as in FIG. 1 and the products withdrawn in solution. The gaseous take-off from the quench tower, typically containing oxygen, hydrogen, carbon monoxide, carbon dioxide, methane, ethane, ethylene, propane and propylene, is fed to a selective oxidation reactor. As previously indicated, it is generally essential for the efficient operation of such a reactor to heat the gas mixture prior to introduction therein.

A portion of the off-gas from the oxidation reactor is passed to a separator to remove carbon oxides by an undisclosed mechanism. A portion of the separator effluent, which contains light hydrocarbons and hydrogen, is purged, treated to remove propane and propylene and discarded, thereby preventing build-up of by-products in the system. The propane and propylene are combined with the remainder of the oxidator effluent and the remainder of the separator effluent and recycled to the dehydrogenator. It is, of course, necessary for the oxidator to be effective in removing all oxygen from the quench tower effluent to prevent significant loss of effectiveness of the dehydrogenator. It is also necessary for the oxygen feed to be pure oxygen because the use of air or oxygenenriched air would produce a rapid accumulation of nitrogen in the system. This would, in turn, require the purging of a larger portion of the recycle stream with resulting loss of efficiency.

Figure 3:
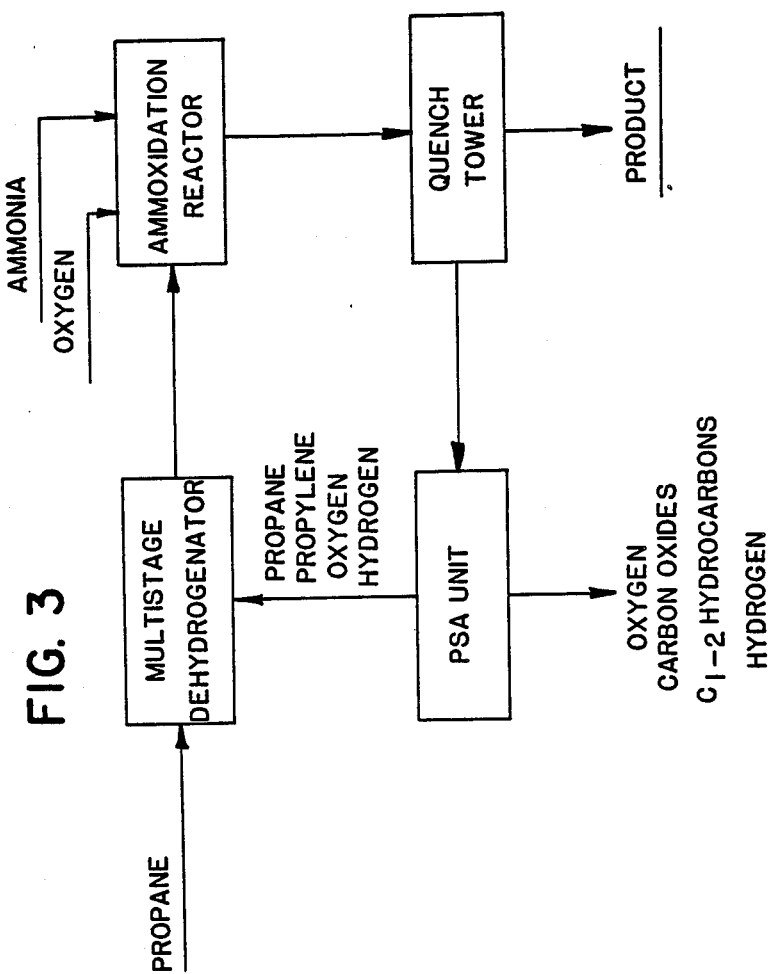
FIG. 3 illustrates in a block diagram the process of the invention for producing acrylonitrile.

The process of the present invention is illustrated in FIG. 3. The present process provides the efficiency of recycle afforded by the process illustrated in FIG. 2, yet does not require the capital cost of oxidation units, does not have a loss of efficiency through a purge stream and does not lose effectiveness of the dehydrogenation catalyst due to oxygen in the recycle stream thereto. In addition, unexpectedly, the process of the present invention can advantageously and efficiently utilize air and oxygen-enriched air as a feed to the ammoxidation reactor.

Referring to FIG. 3, a propane is fed into the multistage dehydrogenator where it is converted to propylene. For increased catalyst lift, it is preferred to introduce a hydrogen-containing gas into the dehydrogenator with the propane feed. The dehydrogenator will be discussed in detail below. The catalyst utilized in the dehydrogenator can be any conventional dehydrogenation catalyst, preferably one or more Group VIII noble metals such as platinum on an alumina support. The effluent product stream from the dehydrogenator comprising unreacted propane, propylene and hydrogen, is fed into a conventional ammoxidation reactor along with pure oxygen, air or, preferably oxygen-enriched air and ammonia.

The ammoxidation reactor utilized in the present process is conventional and may employ either a fixed or fluidized catalyst bed. A typical example of an ammoxidation reactor is disclosed in Angstadt et al., U.S. Pat. No. 4,070,393 and Gates et al., ibid, pp. 381–383, each incorporated herein by reference. The reactor contains a conventional ammoxidation catalyst, such as bismuth-molybdenum oxide, iron-antimony oxide, uranium-antimony oxide precipitated on silica and the like. Other suitable catalysts are disclosed, for example, in *Chemistry of Catalytic Processes*, Gates et al, McGraw Hill (1979) pp 349-350, and Yoshino et al, U.S. Pat. No. 3,591,620, incorporated herein by reference. Additional suitable catalysts are known to those skilled in the art.

The ammoxidation reaction is conducted at a temperature of from about 375° to 550° C., preferably from about 400° to 500° C., at low pressures, typically in the range of from about 3 to 30 psig, preferably from about 5 to 20 psig. The reactants are passed through the reactor at a relatively low velocity, typically in the range of from about 1.75 to 2.2 ft./sec. The oxygen feed may be pure oxygen, air or oxygen-enriched air. In accordance with this invention, oxygen-enriched air preferably contains from about 30 to about 80, most preferably from about 55 to 65, percent by volume of oxygen. Such mixtures may be produced by adjusting the capacity of a conventional oxygen-producing unit, e.g. a conventional pressure swing adsorption unit, or by mixing pure oxygen with air in the proper proportions. The ratio of oxygen to propylene in the feed is suitably in the range of from about 1.6:1 to 2.4:1 by volume. The ratio of ammonia to propylene in the feed is suitably in the range of from about 0.7 to 1.1:1 by volume.

The ammoxidation reaction results in the production of a major amount of acrylonitrile and minor amounts of acrolein, hydrogen cyanide, acetonitrile, carbon oxides and nitrogen, when present in the feed, as well as unreacted oxygen, propylene and propane. This gaseous mixture is quenched or scrubbed with a liquid, such as water, to dissolve the water-soluble compounds for subsequent separation and recovery of acrylonitrile, acetonitrile and hydrogen cyanide.

The gas phase effluent from the quench step is introduced into a pressure swing adsorption (PSA) unit. PSA is a well known process for separating the components of a mixture of gases by virtue of the difference in the degree of adsorption among them on a particular adsorbent retained in a stationary bed. Typically, two or more such beds are operated in a cyclic process comprising adsorption under relatively high pressure and desorption or bed regeneration under low pressure or vacuum. The desired component or components may be obtained during either of these stages. The cycle may contain other steps in addition to the fundamental steps of adsorption and regeneration, and it is commonplace to have two or more adsorbent beds cycled out of phase to assure a pseudo continuous flow of desired product. It is preferred to pass the quench tower effluent through a conventional dryer (not shown) to remove moisture therefrom prior to introducing it into the PSA unit.

It is necessary to raise the pressure of the quench tower effluent in a compressor or other suitable means (not shown) prior to introducing it into the PSA unit. The compressor increases the pressure of the quench tower gaseous effluent to the operating pressure of a PSA unit, typically from about 3 to 50 psig, preferably from about 20 to 40 psig. These ranges may vary to an extent depending on the adsorbent in the PSA unit.

The adsorbent in the PSA unit may be any art-recognized material which will adsorb propane and propylene to a substantially greater degree than carbon oxides, nitrogen and oxygen, or vice versa. Silica gel or a conventional molecular sieve material, such as 4A zeolite, are preferred adsorbent materials. Silica gel is a particularly preferred material wherein oxygen-enriched air is utilized as a reactor feed material.

The PSA unit produces a recycle stream and a waste stream. The latter is comprised of oxygen, carbon oxides, i.e. carbon monoxide and carbon dioxide, nitrogen wherein the feed to the ammoxidation reactor is air or oxygen-enriched air, and $C_{1-2}$ hydrocarbons, i.e. methane, ethane and ethylene, as well as minor amounts of propane and propylene. The PSU recycle stream contains propane, propylene and a minor quantity of oxygen, typically not more than about 3 percent by volume and a minor quantity of nitrogen. The oxygen content in the recycle stream would ordinarily have an adverse effect on the efficiency of the dehydrogenator. This is readily apparent, for example, from the Khoobiar et al patent discussed above wherein it is required that the effluent from the quench tower be fed into a selective oxidation reactor.

The use of an adsorbent in the PSA unit which will adsorb propane and propylene, such as a silica gel, will cause substantially all of the hydrogen in the quench tower effluent to be removed with the waste stream. Therefore, it is necessary to add an appropriate quantity of hydrogen to the propane/propylene recycle stream before introducing it into a latter stage of the dehydrogenator. If an adsorbent which adsorbs carbon oxides and oxygen, such as 4A zeolite molecular sieve, is used as the adsorbent in the PSA unit, the hydrogen will be withdrawn in the recycle stream. Therefore, it will not be necessary to add hydrogen thereto. In fact, it may be necessary to remove some hydrogen therefrom to prevent excessive build-up in the system.

In a preferred embodiment of the subject process, a PSA system comprising parallel PSA units, each containing one of the two types of adsorbers mentioned above, is utilized wherein the feed is disproportionately divided between them so that the combined effluents contain the desired amount of hydrogen. The waste streams from the two units are combined and discarded. The amount of hydrogen required in the recycle feed to the dehydrogenator will vary with the catalyst and can be determined by operation of the system utilizing a given catalyst.

Figure 4:
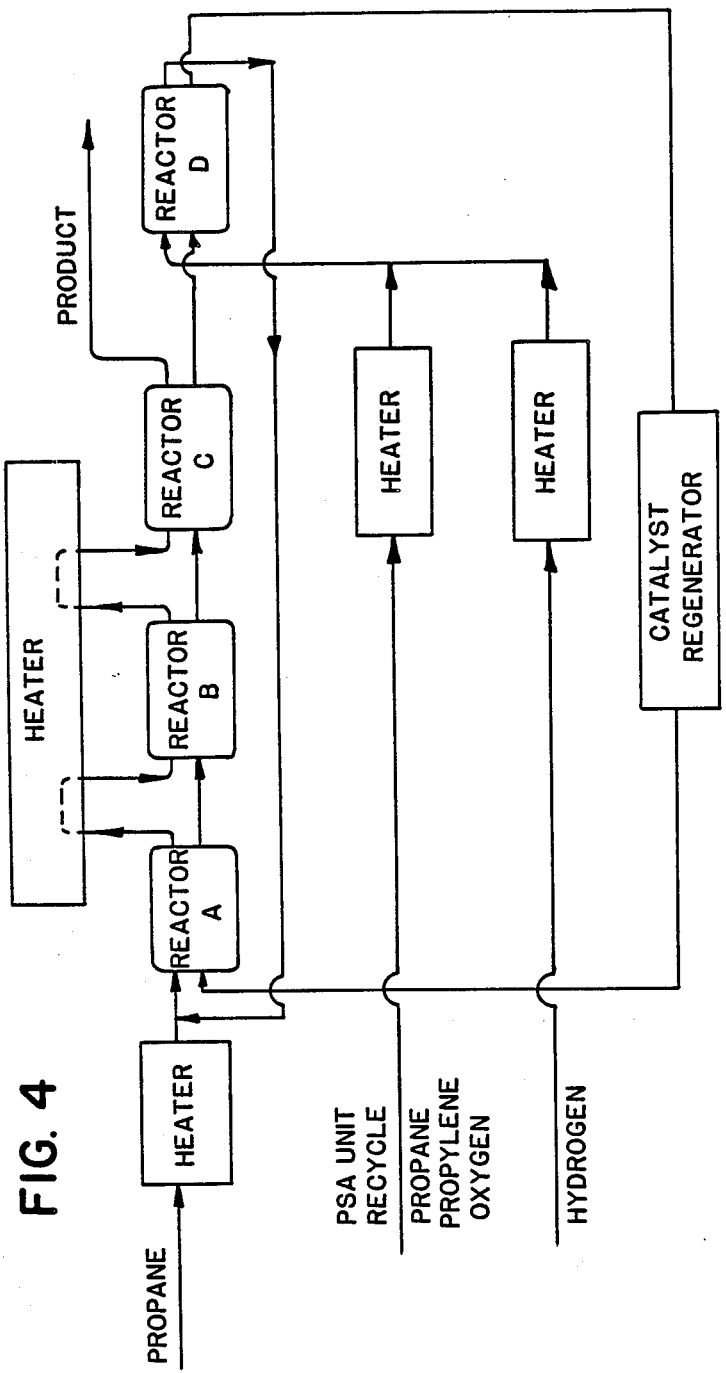
FIG. 4 illustrates in a block diagram detail of the dehydrogenator utilized in the process of this invention.

As shown in FIG. 4, the present invention utilizes a multistage dehydrogenator which is efficient and which, modified in accordance with the present invention, eliminates the need for the selective oxidation reactor in the Khoobiar et al process. The use of a multistage catalytic reactor is described in the literature, e.g. Pujado et al in a paper entitled "Catalytic Conversation of LPG" presented at the American Institute of Chemical Engineers, Apr. 6-10, 1986. In such reactors, the catalyst sequentially flows through a series of discrete reactors and is withdrawn at the end for regeneration and recycle. The reactant gas stream likewise flows through the reactors and is withdrawn into a heating means between each of the individual reactors. The dehydrogenator typically operates at a temperature of from about 500° C. to 800° C., preferably from about 600° C. to 700° C. The reheating of the reactant stream as it flows through the reactors is especially beneficial for an endothermic reaction such as the conversion of propane to propylene.

In accordance with the present invention, the reactant gas stream does not flow through all reactors, but is withdrawn as a product stream from a reactor intermediate the first and last reactors. Preferably, there are at least four reactors and the product stream is withdrawn from the penultimate reactor. It is beneficial to withdraw the product stream from a latter stage of the dehydrogenator to obtain maximum efficiency therefrom. The reheating of the reactant stream takes place only up to and including the reactor from which the product stream is withdrawn.

Applicants have found that if the recycle stream from the PSA unit, which is comprised of unreacted alkane and alkene and minor amounts of oxygen and nitrogen, if present, is introduced into the reactor following that from which the product is withdrawn, passed therethrough and through subsequent reactors, if any, the low oxygen content thereof can be eliminated without detriment to the system. As is evident from FIG. 4, the initial propane feed passes through reactors A through C and is thereafter withdrawn for passage to the ammoxidation reactor, see FIG. 3. The recycle stream from the PSA unit is heated, introduced into reactor D and thereafter introduced into the process as described above. The spent catalyst withdrawn from reactor D is passed through a conventional catalyst regenerator and returned to reactor A. In the regenerator, accumulated carbon is burned off of the catalyst after which it is chemically reduced.

In the embodiment illustrated in FIG. 4, the effluent from the final reactor of the dehydrogenator is introduced into the initial feed stream. In the event that the feed to one of the intermediate reactors more closely approximates the effluent in regard to the concentration of the alkene than the initial feed, the effluent is introduced into such intermediate reactor. It is further contemplated herein to introduce the effluent from the final reactor directly to the ammoxidation reactor if the propylene content thereof is sufficiently high. This might occur, for example, when the PSA effluent passes through two or more reactors of the dehydrogenator.

In the event that the recycle stream from the PSA unit contains no hydrogen, it is combined with a hydrogen-containing stream at elevated temperature and passed through reactor D. The resulting oxygen-free effluent is introduced into the initial feed, an intermediate reactor or the ammoxidation reactor. In the event that the effluent is not introduced into the initial feed, it is necessary to add hydrogen to the initial feed to prolong the life of the catalyst. It will be appreciated by those skilled in the art that a single heater can be utilized in FIG. 4 with all streams flowing therethrough. Further, the hydrogen-containing stream in FIG. 4 can be a stream of medium purity hydrogen obtained from an external source, or a recycle hydrogen stream from within the process. The hydrogen added to the initial feed can likewise be recycled or obtained from an external source. Hydrogen may also be supplied to the heater in combination with an oxygen feed for combustion.

Hydrogen recycle can be obtained from a stream also containing propane and propylene produced by the PSA unit in the event that adsorbent therein adsorbs carbon oxides and oxygen as described above. Hydrogen recycle can also be obtained in the same manner from the product stream of the dehydrogenator before it is introduced into the ammoxiation reactor. It is preferred, as stated previously, to utilize a PSA system containing parallel PSA units each containing a different adsorbent and combining their effluents into a recycle stream containing the proper amount of hydrogen.

Utilizing a sytem as shown in FIG. 3 for the production of acrylonitrile utilizing propane as the starting material, the flow rates at various points in the system were determined and are presented in Table I. The flow rates are expressed in mole percent based on 100 moles of acrylontrile produced. The propane feed was virtually 100 percent propane, and the feed to the ammoxidation reactor was 32.88 percent of ammonia and 67.12 percent of pure oxygen.

In Table I, Point A is the feed into the dehydrogenator after the stream from the final stage thereof has been combined with fresh propane, Point B is the combined feed into the ammoxidation reactor, Point C is the ammoxidation reactor effluent, Point D is the quench tower gaseous effluent, Point E is the recycle stream from the PSA unit and Point F is the PSA unit waste stream.

TABLE I

| Component | A | B | C | D | E | F |
|---|---|---|---|---|---|---|
| Propylene | 15.7 | 20.3 | 7.7 | 15.5 | 24.0 | 3.5 |
| Propane | 75.0 | 21.0 | 19.4 | 38.8 | 61.8 | 8.9 |
| Oxygen | 0.1 | 27.2 | .5.0 | 1.0 | 0.2 | 22.5 |
| CO | 0.9 | 0.4 | 1.1 | 1.4 | 1.4 | 1.3 |
| $CO_2$ | 3.1 | 1.4 | 3.5 | 4.4 | 4.7 | 4.1 |
| Acrylonitrile | — | — | 9.8 | — | — | — |
| Acrolein | — | — | 0.1 | — | — | — |
| Acetonitrile | — | — | 0.1 | — | — | — |
| HCN | — | — | 1.5 | — | — | — |
| Water | — | — | 35.6 | — | — | — |
| Ammonia | — | 13.3 | 1.0 | — | — | — |
| Methane | 3.5 | 2.3 | 2.2 | 4.3 | 5.3 | 3.0 |
| Ethane | 0.7 | 0.5 | 0.4 | 0.9 | 1.1 | 0.6 |
| Ethylene | 0.7 | 0.5 | 0.4 | 0.9 | 1.1 | 0.6 |
| Hydrogen | 0.3 | 13.1 | 12.2 | 24.3 | 0.4 | 55.4 |

Again utilizing a system as shown in FIG. 3 for the production of acrylonitrile with propane as a starting material, the oxygen feed to the ammoxiation reactor was changed to a mixture of equal part of pure oxygen and air which produced oxygen-enriched air containing approximately 60 percent of oxygen. The flow rates at the various points in the system were determined utilizing 100 percent air as the oxygen-containing gas and are also presented in Table II. The data expressed in Table II represents operation of the system under conditions such that 60 percent and 80 percent, respectively, of the propylene in the ammoxidation reactor is converted therein to different products, including acrylonitrile.

TABLE II

| Component | A | B | C | D | E | F |
|---|---|---|---|---|---|---|
| 60 Percent Conversion - Equal parts pure oxygen and air ||||||| 
| Propylene | 17.4 | 12.7 | 7.2 | 4.8 | 25.9 | 0.5 |
| Propane | 76.5 | 12.7 | 12.0 | 18.0 | 64.8 | 1.2 |
| Oxygen | — | 19.4 | 5.0 | 7.5 | 0.3 | 10.1 |
| CO | — | — | 0.5 | 0.8 | — | 1.1 |
| $CO_2$ | 4.3 | 1.2 | 2.8 | 2.4 | 6.4 | 1.0 |
| Acrylonitrile | — | — | 6.0 | — | — | — |
| Acrolein | — | — | 0.1 | — | — | — |
| Acetonitrile | — | — | 0.1 | — | — | — |
| HCN | — | — | 1.2 | — | — | — |
| Water | — | — | 23.8 | — | — | — |
| Ammonia | — | 8.7 | 1.0 | — | — | — |
| Methane | — | 0.4 | 0.4 | 0.6 | 0.1 | 0.8 |
| Ethane | — | 0.1 | 0.1 | 0.1 | — | 0.2 |
| Ethylene | — | 0.1 | 0.1 | 0.1 | — | 0.2 |
| Hydrogen | 0.3 | 8.0 | 7.5 | 11.3 | 0.4 | 15.2 |
| Nitrogen | 1.3 | 36.7 | 34.6 | 51.9 | 2.0 | 69.8 |
| 80 Percent Conversion - Equal parts pure oxygen and air |||||||
| Propylene | 7.4 | 9.8 | 1.9 | 2.8 | 11.7 | 0.2 |
| Propane | 85.1 | 12.8 | 12.1 | 18.4 | 76.2 | 1.2 |
| Oxygen | — | 20.2 | 5.0 | 7.6 | 0.3 | 9.8 |
| CO | — | — | 0.7 | 1.0 | — | 1.3 |
| $CO_2$ | 5.6 | 1.4 | 3.2 | 2.9 | 8.8 | 1.1 |
| Acrylonitrile | — | — | 6.0 | — | — | — |
| Acrolein | — | — | 0.1 | — | — | — |
| Acetonitrile | — | — | 0.1 | — | — | — |
| HCN | — | — | 1.3 | — | — | — |
| Water | — | — | 24.7 | — | — | — |

TABLE II-continued

| Component | A | B | C | D | E | F |
|---|---|---|---|---|---|---|
| Ammonia | — | 8.9 | 1.0 | — | — | — |
| Methane | 0.1 | 0.4 | 0.4 | 0.6 | 0.1 | 0.8 |
| Ethane | — | 0.1 | 0.1 | 0.1 | — | 0.2 |
| Ethylene | — | 0.1 | 0.1 | 0.1 | — | 0.2 |
| Hydrogen | 0.3 | 8.0 | 7.5 | 11.5 | 0.5 | 14.8 |
| Nitrogen | 1.5 | 38.2 | 35.9 | 54.8 | 2.4 | 70.5 |
| 60 Percent Conversion - Air | | | | | | |
| Propylene | 17.1 | 8.4 | 3.2 | 4.2 | 25.0 | 0.3 |
| Propane | 74.8 | 8.4 | 8.1 | 10.5 | 62.6 | 0.6 |
| Oxygen | — | 14.8 | 5.0 | 6.5 | 0.4 | 7.7 |
| CO | — | — | 0.4 | 0.6 | — | 0.7 |
| $CO_2$ | 4.8 | 0.9 | 2.1 | 1.6 | 7.1 | 0.6 |
| Acrylonitrile | — | — | 3.9 | — | — | — |
| Acrolein | — | — | — | — | — | — |
| Acetonitrile | — | — | — | — | — | — |
| HCN | — | — | 0.9 | — | — | — |
| Water | — | — | 16.2 | — | — | — |
| Ammonia | — | 6.1 | 1.0 | — | — | — |
| Methane | — | 0.3 | 0.3 | 0.4 | 0.1 | 0.4 |
| Ethane | — | 0.1 | 0.1 | 0.1 | — | 0.1 |
| Ethylene | — | 0.1 | 0.1 | 0.1 | — | 0.1 |
| Hydrogen | 0.3 | 5.2 | 5.0 | 6.4 | 0.4 | 7.6 |
| Nitrogen | 3.0 | 55.8 | 53.6 | 69.6 | 4.4 | 82.1 |
| 80 Percent Conversion - Air | | | | | | |
| Propylene | 7.3 | 6.5 | 1.3 | 1.6 | 11.3 | 0.1 |
| Propane | 83.5 | 8.5 | 8.2 | 10.7 | 73.9 | 0.6 |
| Oxygen | — | 15.0 | 5.0 | 6.5 | 0.5 | 7.5 |
| CO | — | — | 0.5 | 0.6 | — | 0.7 |
| $CO_2$ | 5.5 | 0.9 | 2.2 | 1.7 | 8.5 | 0.6 |
| Acrylonitrile | — | — | 4.1 | — | — | — |
| Acrolein | — | — | — | — | — | — |
| Acetonitrile | — | — | 0.1 | — | — | — |
| HCN | — | — | 0.9 | — | — | — |
| Water | — | — | 16.7 | — | — | — |
| Ammonia | — | 6.3 | 1.0 | — | — | — |
| Methane | 0.1 | 0.3 | 0.3 | 0.4 | 0.1 | 0.4 |
| Ethane | — | 0.1 | 0.1 | 0.1 | — | 0.1 |
| Ethylene | — | 0.1 | 0.1 | 0.1 | — | 0.1 |
| Hydrogen | 0.3 | 5.3 | 5.1 | 6.7 | 0.5 | 7.7 |
| Nitrogen | 3.3 | 57.0 | 54.7 | 71.6 | 5.2 | 82.3 |

The process of this invention is advantageous in that it is very efficient and is cost attractive in comparison to prior art processes requiring a selective oxidation unit. In addition, the process of the invention has a comparatively small incidence of build-up of any of the components of the various gaseous streams formed or separated at any stage thereof. Further, the subject process can be utilized with air or oxygen-enriched air as a feed to the ammoxidation reactor, heretofore not feasible with a closed loop system. Unexpectedly, the subject process operates at particularly enhanced efficiency with an oxygen-enriched air feed.

The invention has been described with reference to preferred embodiments thereof. It will be appreciated by those skilled in the art that various modifications may be made from the specific details given without departing from the spirit and scope of the invention.

We claim:

1. A process for the production of alpha,beta olefinically unsaturated nitriles comprising:
   (a) forming an alkene from a gaseous alkane by passage through a multistage catalystic dehydrogenator comprised of a series of at least three discrete catalystic reactors, wherein the product stream containing said alkene and unreacted alkane is withdrawn from a reactor intermediate the first and last of said reactors, the gaseous flow between said reactors, including the reactor from which the product stream is withdrawn, is passed through a heating means to raise the temperature thereof, and the catalyst in the dehydrogenator is passed through all of said reactors, regenerated and recycled to the first reactor;
   (b) introducing a gaseous stream comprising said alkene, pure oxygen, air or a gas-enriched in oxygen relative to air and ammonia into a suitable reactor and reacting them in the vapor phase in the presence of an ammoxidation catalyst to produce a gaseous effluent containing said nitrile;
   (c) quenching said effluent in a liquid to form a liquid phase containing said nitrile and a gaseous phase;
   (d) recovering said nitrile from the liquid phase;
   (e) introducing the gaseous phase under pressure into a pressure swing adsorption unit to thereby form (i) a gaseous stream comprising said unreacted alkane and alkene, a minor amount of oxygen and nitrogen when air or oxygen-enriched air is introduced into the reactor in step (b) and (ii) a waste stream comprising oxygen, carbon monoxide, carbon dioxide, hydrocarbons lower than the reactant alkane, nitrogen when air or oxygen-enriched air is introduced into the reactor in step (b) and minor amounts of unreacted alkane and alkene;
   (f) introducing said gaseous stream into the reactors in said dehydrogenator which follow in sequence the reactor from which the product stream was withdrawn, thereby removing substantially all of the oxygen contained in said stream; and
   (g) introducing the effluent from said last reactor into said first reactor; a reactor other than said first reactor wherein the concentration of the alkene is approximately the same as that of said effluent; or said reactor in step (b).

2. A process in accordance with claim 1, wherein the dehydrogenator contains at least four reactors and the product stream is withdrawn from the penultimate reactor.

3. A process in accordance with claim 1, wherein the alkane is propane, the alkene is propylene and the nitrile produced is acrylonitrile.

4. A process in accordance with claim 1, wherein oxygen is added in step (b) as pure oxygen.

5. A process in accordance with claim 1, wherein oxygen is added in step (b) as oxygen-enriched air containing from about 30 to about 80 percent of oxygen by volume and the stream produced in step (e) additionally contains a minor amount of nitrogen.

6. A process in accordance with claim 5, wherein the oxygen-enriched air contains from about 55 to about 65 percent by volume of oxygen.

7. A process in accordance with claim 1, wherein the gaseous phase in step (d) is introduced into the pressure swing absorption unit at a pressure of from about 3 to 50 psig.

8. A process in accordance with claim 1, wherein oxygen is introduced into the reactor in step (b) as oxygen-enriched air and said pressure swing adsorption unit removes substantially all of the hydrogen from the quench tower effluent and said gaseous stream in step (f) is combined with a hydrogen-containing stream prior to introduction into said reactor.

9. A process in accordance with claim 1, wherein the adsorbent in the pressure swing adsorption unit is a silica gel or a molecular sieve.

10. A process in accordance with claim 1, wherein oxygen is introduced into the reactor in step (b) as pure oxygen and the gaseous stream formed in step (e) contains substantially all of the hydrogen in the quench tower effluent and said stream is treated to remove excess hydrogen prior to introduction into said reactor.

11. A process in accordance with claim 10, wherein at least a portion of said removed hydrogen is recycled to said process.

12. A process in accordance with claim 1, wherein the effluent in step (g) is introduced into the feed to said first reactor.

13. A process in accordance with claim 1, wherein the effluent in step (g) is introduced into a reactor other than said first reactor wherein the concentration of the alkene is approximately the same as that of said effluent.

14. The process in accordance with claim 1, wherein the effluent in step (g) is introduced into said reactor in step (b).

15. A process in accordance with claim 1, wherein hydrogen is recovered from the product stream withdrawn from the dehydrogenator prior to introduction into said reactor in step (b) and recycled to said process.

16. A process in accordance with claim 1, wherein the temperature in the dehydrogenator is from about 500° to 800° C.

17. A process in accordance with claim 1, wherein, in step (e), the gaseous phase is divided and the resultant divided streams are introduced into two pressure swing adsorption units operating in parallel, each containing a different adsorbent such that the gaseous stream formed in one of said pressure swing adsorption units contains the hydrogen in said gaseous phase, whereas the gaseous stream formed in the other pressure swing adsorption unit contains no hydrogen, wherein the gas phase is divided disproportionately between said pressure swing adsorption units so that the gaseous streams formed by said pressure swing adsorption units, when combined, contain a predetermined concentration of hydrogen.

18. A process in accordance with claim 17, wherein said pressure swing adsorption unit which produces a hydrogen-containing stream contains a 4A zeolite molecular sieve adsorbent and the other pressure swing adsorption unit contains a silica gel adsorbent.

* * * * *